United States Patent [19]

Lee

[11] 4,352,662
[45] Oct. 5, 1982

[54] DENTAL ARTICULATOR FRAMES AND METHOD OF MAKING

[76] Inventor: Robert L. Lee, 22937 Grand Ter., Colton, Calif. 92324

[21] Appl. No.: 221,056

[22] Filed: Dec. 29, 1980

Related U.S. Application Data

[63] Continuation of Ser. No. 965,049, Nov. 30, 1978, abandoned, which is a continuation-in-part of Ser. No. 814,815, Jul. 11, 1977, Pat. No. 4,209,909, which is a continuation-in-part of Ser. No. 581,203, May 27, 1975, Pat. No. 4,034,475, which is a continuation-in-part of Ser. No. 485,158, Jul. 1, 1974, Pat. No. 4,034,474.

[51] Int. Cl.³ .................................................. A61C 11/00
[52] U.S. Cl. ..................................... 433/56; 29/160.6; 433/57
[58] Field of Search ...................... 433/54, 55, 56, 57, 433/58, 59, 60, 61, 62, 63, 64, 65, 66, 67, 73; 29/558, 160.6; 408/1 R

[56] References Cited

U.S. PATENT DOCUMENTS

| | | | |
|---|---|---|---|
| 1,733,507 | 10/1929 | McCollum | 433/56 |
| 2,816,360 | 12/1957 | Stuart | 433/55 |
| 3,019,530 | 2/1962 | DePietro | 433/59 |
| 3,052,030 | 9/1962 | Spence | 433/73 |
| 3,160,955 | 12/1964 | DePietro | 433/56 |
| 3,206,852 | 9/1965 | Swanson | 433/57 |
| 3,224,096 | 12/1965 | Stuart | 433/56 |
| 3,452,439 | 7/1969 | Lee | 433/55 |
| 3,593,424 | 7/1971 | Lee | 433/55 |
| 3,694,919 | 10/1972 | Lee et al. | 433/56 |
| 3,896,550 | 7/1975 | Lee | 433/56 |
| 4,045,872 | 9/1977 | Arant | 433/55 |

Primary Examiner—Gene Mancene
Assistant Examiner—John J. Wilson
Attorney, Agent, or Firm—Knobbe, Martens, Olson, Hubbard & Bear

[57] ABSTRACT

The frames and guide blocks for a dental articulator are precisely machined in three dimensions to guarantee interchangeability with other frames and guide blocks and accuracy of articulator movement with respect to dental casts mounted thereon. Test blocks for checking accuracy of the articulator are provided. Also disclosed is a plate removeably mounted on the guide block having a curve thereon indicating the curvature of an opening in the guide block.

17 Claims, 10 Drawing Figures

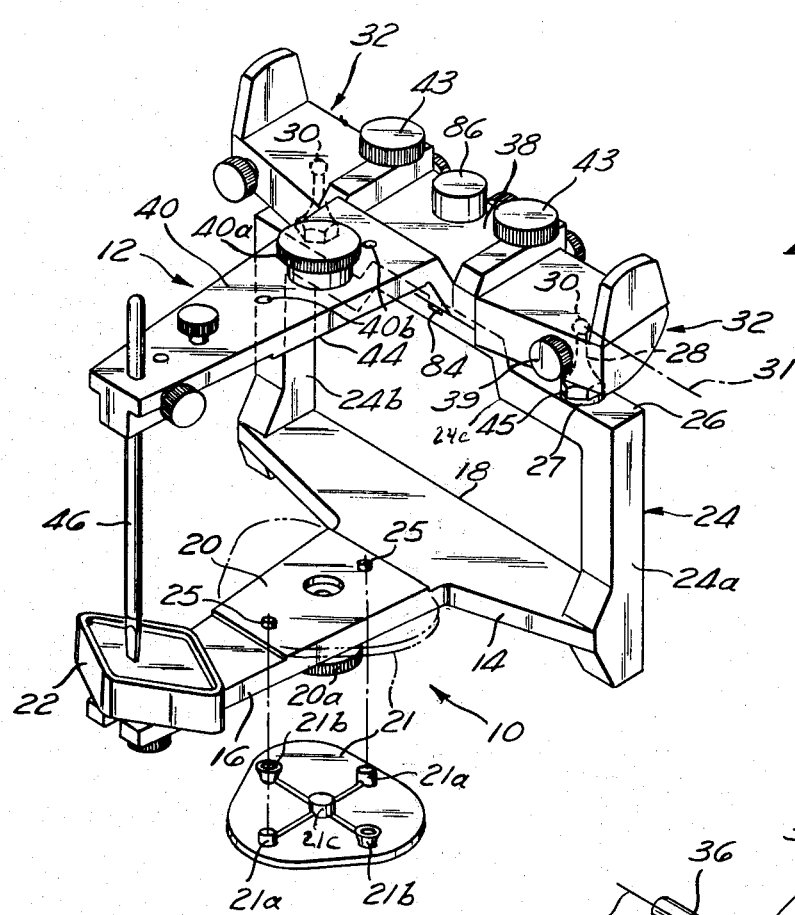
Fig. 1
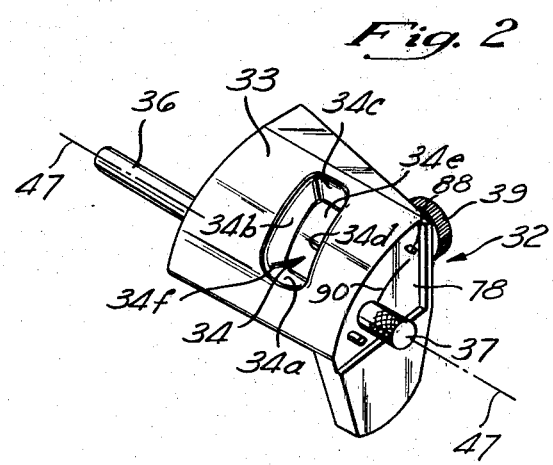
Fig. 2
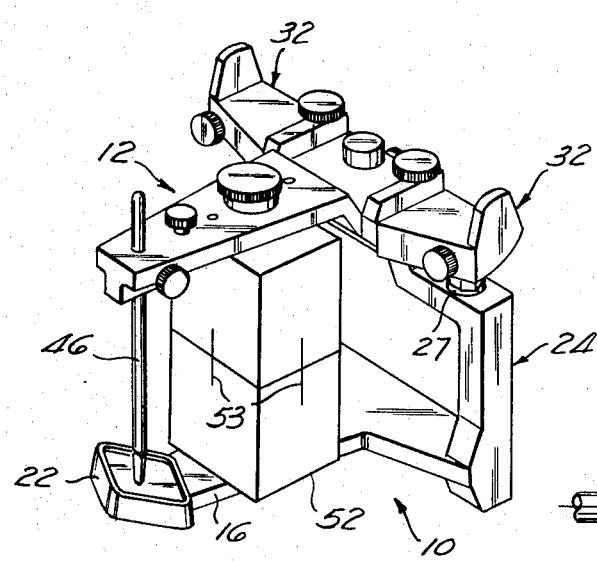
Fig. 6
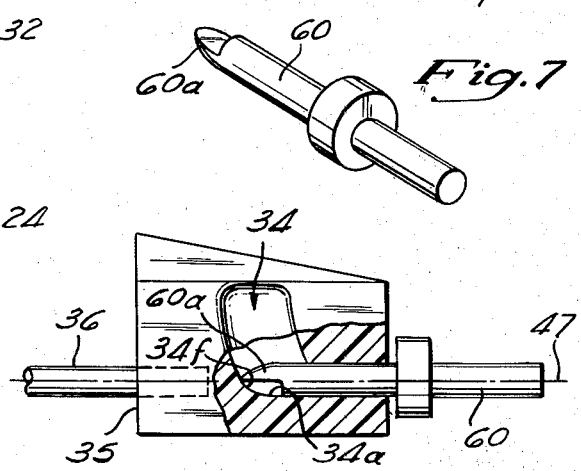
Fig. 7
Fig. 8

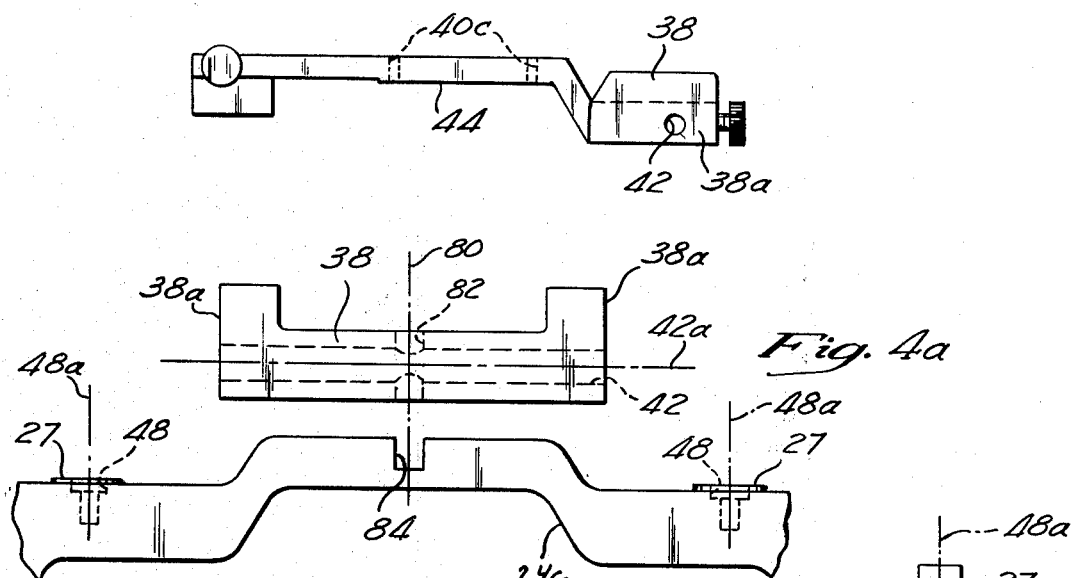
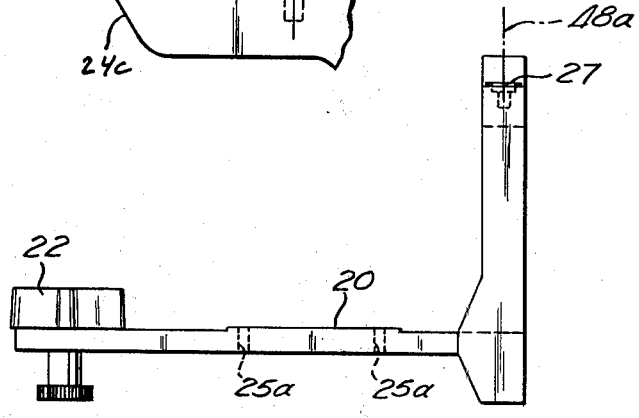
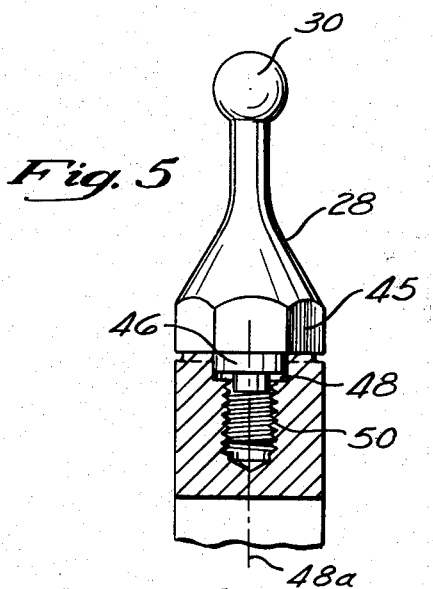
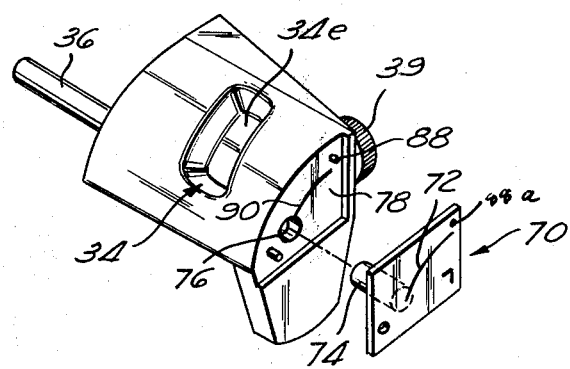

DENTAL ARTICULATOR FRAMES AND METHOD OF MAKING

CROSS-REFERENCE TO RELATED PATENTS AND APPLICATIONS

This application is a continuation of application, Ser. No. 965,049, filed Nov. 30, 1978, and now abandoned, which is a continuation-in-part of application, Ser. No. 814,815, filed July 11, 1977, now U.S. Pat. No. 4,209,909 which issued July 1, 1980, which is a continuation-in-part of Ser. No. 581,203, filed May 27, 1975, now U.S. Pat. No. 4,034,475 which issued July 12, 1977, which is in turn a continuation-in-part of Ser. No. 485,158, filed July 1, 1974, now U.S. Pat. No. 4,034,474 which also issued July 12, 1977.

BACKGROUND OF THE INVENTION

The present invention relates to dental articulators and, more particularly, to an improved articulator which allows for accurate interchangeability of dental casts.

The purpose of a dental articulator is to simulate the jaw or condylar movements of a patient. This instrument enables a dentist to obtain the necessary diagnostic information for the treatment of occlusal irregularities, such as malocclusion, and the fabrication of dental casts or "dentures". In U.S. Pat. No. 3,452,439, issued to Robert L. Lee on July 1, 1969, there is described a system of jaw movement simulation wherein the dynamic movement of a patient's jaws is recorded, and from this information plastic blocks are formed. These blocks have three-dimensional openings or pathways cut therein that may be used with a dental articulator to simulate or almost duplicate the particular patient's jaw movement.

In the above-referenced U.S. Pat. Nos. 4,034,474 and 4,034,475, there is disclosed a simplified system for measuring jaw movements, with such information being useful in setting and operating dental articulators. It is further suggested in those patents that plastic guide blocks of the type disclosed in the earlier Lee patent be classified according to certain characteristics of jaw movements to provide a series of average value blocks from which the pair most closely fitting the measurements of a particular patient's condylar movements may be selected. Such guide blocks have curved walls which produce movement that closely simulates a patient's particular condylar movements, thus enabling a dentist to treat accurately an occlusal or denture problem without requiring the presence of the patient.

In the fabrication and use of dental casts, it is often necessary to transfer the cast from one articulator to another several times. Typically, a dentist or his assistant will take a mold of the patient's teeth and then give the mold to a lab technician for the preparation of the dental cast. Thus, it is important that the articulators be interchangeable to obtain consistent results.

In the past, differences in dimensional characteristics between articulators were largely ignored, thus leading to inaccuracies in the making and using of dental casts. Even small dimensional differences in articulators are crucial since small irritations caused by inaccurate dentures are easily detected in the mouth.

Certain manufacturers of articulators attempt to overcome this problem by providing auxiliary equipment, such as binoculars and cross-hairs, in order to accurately adjust the mounting of a cast in an articulator to eliminate the effect of dimensional irregularities among articulators. These devices, however, are costly and require more of a dentist's or lab technician's time.

SUMMARY OF THE INVENTION

The dental articulator of the present invention eliminates the need for auxiliary equipment and insures that dental casts can be accurately transferred from one articulator to another with identical results obtained by merely mounting the cast on the mounting pad without adjustment.

The lower frame of one type of articulator has an upwardly facing area for the mounting of the dental cast of the lower jaw or mandible of the patient. An upper frame of the articulator, disposed above the lower frame, has a similar area for mounting the dental cast of the upper jaw of a patient's maxilla. The upper frame is supported by a portion of the lower frame which is vertical and which makes contact with the upper frame by means of a pair of spherical styluses. The styluses are mounted atop pedestals which are attached to the upper surface of a vertical portion of the lower frame, and the styluses are inserted into guide blocks supported on the rear of the upper frame. The dental casts can then be easily observed by moving the upper frame relative to the lower frame within the restraints allowed by the guide block-stylus joint.

In order to achieve interchangeability among articulators, accurate relationships are required between certain structural members. The dental cast mounting area of the lower frame and the upper surface of the vertical portion of the lower frame must be maintained structurally consistent with respect to each other from one articulator to another. Thus, if these surfaces are spaced and parallel to one another in one articulator, they should also be spaced and parallel to a high degree of accuracy in another articulator. Also, the pedestals and styluses themselves must be uniform both within one articulator and among all articulators. Thus, there should be an accurate and consistent relationship between a line formed between the centers of the styluses and the plane formed by the mounting area of the lower frame.

Similarly, with respect to the upper frame, there should be maintained a consistent and accurate structural relationship between the mounting area and the point of contact of the styluses with the guide blocks. Thus, it is important that the guide blocks be accurately mounted on the upper frame such that a line through the point of contact with the styluses is also parallel to the mounting area. To this end, the mounting holes into which the guide block mounting pins are inserted must be maintained structurally consistent with the plane formed by the mounting area. In other words, a line through the center of the mounting holes should be parallel to the planes formed by the mounting area of the upper frame.

The relationship between the mounting area of the lower frame and the upper surface of the vertical portion of the lower frame is maintained parallel to a high degree of accuracy by machining those surfaces either simultaneously or without moving the casting in a holding device. The machining is performed when the frame is a one-piece construction, preferably of a single casting. This construction is advantageous over articulators having separate lower and vertical frame portions which must be machined independently and then joined by fasteners or welding. The accurate relationship between the mounting area and the upper surface of the lower frame is also crucial in obtaining interchangeability among articulators which do not utilize the guide block-stylus type of hinging apparatus.

The structural relationship between the mounting area of the upper frame and the centerline of the guide block mounting hole is also maintained parallel to a high degree of accuracy due to the machining and drilling of these surfaces to close tolerances. Again, the one-piece construction of the upper frame increases the accuracy of its construction.

Another advantage of the present invention is found in the construction of the pedestals which support the styluses on the upper surface of the lower frame. It is imperative that the styluses be uniformly positioned on each articulator in order to insure interchangeability among articulators. To achieve this, on the lower portion of each pedestal is found a cylindrical sleeve which is mated to a close tolerance into a recessed area in the upper surface. This construction prohibits the pedestal from moving laterally with respect to the other pedestal, since a threaded attachment alone would not give a sufficiently rigid support to the pedestal.

The sockets in the lower frame on which the pedestals are mounted are precisely spaced from each other and from alignment dowel holes formed in the dental cast mounting area of the lower frame. Also these holes are positioned accurately with respect to a centric locating slot. The upper frame is similarly provided with a precisely located hole for receiving a centric pin that mates with the slot in the lower frame. The upper frame is also provided with dowel holes in its dental cast mounting area that are accurately located with respect to the holes in the upper frame and with respect to end surfaces on the rear portion of the upper frame.

Guide blocks mounted on the upper frame of the articulator each have an opening formed therein for receiving a stylus, and the rear wall and adjacent medial and upper wall portions of such opening are precisely formed to provide accuracy and interchangeability with respect to the hinge axis. This accuracy is attained by drilling a hole through the outer wall of a guide block on a line concentric with the mounting pin for the guide block, and the drill forms the rear wall and adjacent upper wall of the guide block opening. Also, the tip of the drill is curved to form accurately the corner between the rear and medial wall of the opening. This corner and the adjacent rear, upper, and medial wall surfaces are the ones most critical in guiding movement of styluses during use of the articulator.

A further advantage of the present invention is that the base portion of the vertical frame where attachment is made to the rear portion of the lower frame is built-up and strengthened to prevent the articulator from bending, even slightly, due to the movement of the frames relative to each other by the dentist. Such bending might destroy the accurate structural relationships between certain members of the articulator, as described above.

BRIEF DESCRIPTION OF DRAWINGS

These and other advantages are readily apparent from the drawings in which:

FIG. 1 is a perspective view of a dental articulator illustrating the invention;

FIG. 2 is a perspective view of one of the guide blocks showing the guide path;

FIG. 3 is a side view of the lower frame with stylus and pedestal removed;

FIG. 4 is a side view of the upper frame with the guide blocks removed;

FIG. 4a is an enlarged, fragmentary view of the upper and lower frames illustrating hole alignments;

FIG. 5 is a cross-section showing the construction of the pedestal and cylindrical sleeve portion;

FIG. 6 is a perspective view depicting the manner in which the articulator of the present invention is tested for accuracy;

FIG. 7 is a perspective view of a drill bit used for forming the rear wall of a guide block opening;

FIG. 8 is an elevational, partially sectionalized view of a guide block with the drill in its operating position; and FIG. 9 is an exploded, perspective view of a guide block and a curve plate which mounts on the guide block.

DETAILED DESCRIPTION OF THE PREFERRED EMBODIMENT

Referring to FIG. 1, there is shown a dental articulator having a lower frame 10 pivotally supporting an upper frame 12. The lower frame 10 includes a generally horizontal, T-shaped base member 14 having an extended arm 16 and a cross-bar portion 18. Extending vertically from the cross-bar 18 is a bridge-like portion 24. This vertical portion consists of two posts 24a and 24b, which are attached to the extreme ends of the cross bar, and a lateral truss 24c which connects the two posts to form a closed loop. In the preferred embodiment of the present invention, the vertical posts and lateral truss are an integral part of base member 14 and together form a one-piece construction.

The extended arm 16 of the lower frame includes a mounting area 20 found on the upper surface of the arm for the attachment of a dental cast, and an incisal pin rest pad 22. A mounting plate 21 is shown in phantom in FIG. 1 on the mounting area 20, and in solid lines below the mounting area. A pair of alignment dowels 25 extend upwardly from the area 20, and mate with sockets in the upwardly extending pins 21a in the mounting plate 21. Additional buttons 21b on the mounting plate 21 facilitate the plaster connection to a dental cast. A threaded fastener 20a extends through a hole in the mounting surface 20 and threads into a socket in the lower side of the central button 21c in the mounting plate 21 to secure the plate to the area 20.

On the upper surface 26 of lateral truss 24c is found a pair of column-like pedestals 28 which support spherical styluses 30. The pedestals rest on two raised surfaces or bosses 27 which are formed on the upper surface 26 of the vertical portion of the lower frame. The styluses 30 come into contact with guide blocks 32 and together act as a hinge in allowing upper frame 12 to move relative to lower frame 10 in simulating human jaw movement.

Referring to FIG. 2, there is shown the details of a guide block 32 preferably constructed of plastic. On the curved surface 33 of the guide block is formed a three-dimensional guide path 34 that controls the movement of the stylus 30 when received therein. The guide path 34 is provided by rear wall 34a, a medial wall 34b, a forward wall 34c, a lateral wall 34d, and an upper wall 34e. The rear and medial walls are joined by a curved corner 34f having a circular radius. Each guide block has a mounting pin 36 extending from the medial side of the block to allow for attachment of the blocks to the upper frame. A locking pin 37 extends through a hole in the lateral wall concentric with the pin 36. The inner end of the pin 37 is recessed to mate with a stylus 30 to enable the articulator frames to be locked together for simple hinging action. Set screw 39 fixes the pin 37.

Referring again to FIG. 1, the upper frame 12 consists of a rear portion 38 and a forward portion 40 which extends out from the rear portion and is positioned above the extended arm 16 of the lower frame. On the under surface of forward portion 40 is found mounting area 44 for receiving a dental cast. Extending vertically through the tip of the forward portion 40 is an incisal rest pin 46 which rests in pad 22 on the lower frame in order to support the upper frame when no dental casts are mounted in the articulator.

Rear portion 38 of the upper frame is a generally rectangular block having a transverse guide block mounting hole 42 extending from one vertical wall to the other. Guide block mounting hole 42, best seen in FIG. 4, receives the mounting pins 36 of the guide blocks which are then locked into place by set screws 43.

In order to achieve interchangeability among articulators, it is necessary that accurate structural relationships between certain elements of each articulator be maintained. For example, if identical diagnostic results are to be obtained between two articulators, the respective dental cast mounting areas 44 and 20 of the upper and lower frames when connected for simple hinging action and properly spaced, should be parallel to one another to a close tolerance. It can be seen by reference to FIG. 1 that if both mounting areas are independently parallel to an axis 31 through the center of styluses 30, the mounting areas will be parallel to one another, if properly spaced by the pin 46. Thus, with respect to the lower frame, it is necessary that the pedestals 28 and styluses 30 be uniform and mounted to a uniform depth in the upper surface 26 of lateral truss 24c.

Referring to FIG. 3, then, it is necessary to achieve a high degree of parallelism between boss 27 on which the pedestals rest, and mounting area 20. In the preferred embodiment, these surfaces are machined to be parallel simultaneously, or in sequence in a single machining procedure wherein the lower frame is mounted in a holding fixture and a precision milling machine utilized to obtain the desired machining.

In addition to forming the surfaces 20 and 27 accurately parallel and spaced, it is also important that the frame have precision from front to rear and from side to side. Thus, the center lines of the two dowel holes 25a should be accurately located with respect to the center line 48a of precisely located and drilled pedestal receiving sockets 48. Thus, these holes should preferably be formed while the one-piece frame is mounted in a single fixture or jig. Also a slot 84 in the lateral truss of the lower frame, shown in FIG. 4a, should be accurately machined with respect to the holes 25a and 48. Slot 84 need not necessarily be centered, although this is preferable, but in any event it must be accurate to provide interchangeability between articulator frames.

As discussed above, the dentist must move the upper frame relative to the lower frame in simulating the jaw movements of the patient. In doing so, the guide blocks bear against the styluses 30 according to the guide path 34, thus, creating moment forces on the pedestal 28. Movement of the pedestals relative to each other or to the lower frame might destroy accuracy of the articulator; therefore, it is important that the pedestals retain their rigidity and uniform spacing from one articulator to the next.

Accordingly, shown in FIG. 5, is a cross-section of the pedestal and a portion of the lateral truss 24c into which the pedestal is mounted. Beneath the shoulder 45 of the pedestal is a cylindrical sleeve 46 which snugly fits into the precisely located and drilled socket 48 in the upper surface 26 of the lateral truss. Beneath this sleeve are screw threads 50 which provide for attachment of the pedestal to the lateral truss. Utilization of sleeve 46 insures the accurate spacing of the pedestals between each other and the maintenance of their rigidity, which has advantages a threaded attachment alone would not provide. That is, the threads serve only an attaching function rather than a locating function.

In order to withstand the bending forces on the vertical portion of the lower frame, the base portions of posts 24a and 24b are reinforced, as shown in FIG. 3. Again, this construction insures that the accuracy of the articulator of the present invention will not be destroyed in the course of its use.

With respect to the upper frame 12, it is important that hinge axis 31 be parallel to a close tolerance to mounting area 44. With reference to FIG. 4, the center line of guide block pin mounting hole 42 must be parallel to the mounting area 44. This is accomplished by making the upper frame as an integral unit and then machining the surface 44 and drilling the mounting hole in a coordinated operation to provide the necessary accuracy. In a preferred method, the end surfaces 38a on the rear portion 38 are machined precisely parallel to each other, and the pin mounting hole 42 is drilled through the rear portion 38. A snug fitting reference pin (not shown) is then positioned in the hole 42 with a portion extending outwardly to serve as a reference for the machining of the surface 44. The upper frame is then positioned in a fixture and the reference pin located in a cradle (not shown) on a milling machine, followed by the machining of the surface 44. The cradle is precisely located with respect to a reference surface on the fixture so that the surface 44 is precisely parallel to the axis of the hole 42, and the vertical distance between the two is accurate.

As with the lower frame, it is also critical that the two dowel holes 40c in the mounting surface 44 be precisely located laterally with respect to the frame end surfaces 38a, and that they be precisely located from front to rear with respect to the center line 42a of the pin mounting hole 42, as seen from FIGS. 4 and 4a. In addition, the center line 80 of a hole 82 must be precisely parallel to the end surfaces 38a and the dowel holes 40c. The hole 82 must also be accurately located (centered as shown) between the end surfaces 38a to align properly with the slot 84 in the lower frame, which was laterally centered. Note from FIG. 4a that the center line 80 represents the center of both hole 82 and slot 84. It is preferable that these holes in the upper frame be performed while mounted in the same fixture to facilitate accuracy.

A centric pin 86, FIG. 1, fits precisely within the hole 82 and the slot 84 to lock the frames in centric position.

To complete the accurate alignment of the upper frame to the lower frame, it is important that the guide blocks 32 be accurately made and mounted. As indicated above, the mounting pin 36 is collinear with the center line of the locking pin 37. Thus, of course, the hole in which the pin 37 extends should also be collinear and accurately formed. Further, the rear wall 34a and adjacent portion of upper wall 34e in the guide block opening 34 must be accurately formed so that when the upper frame is in centric position with a stylus engaging the rear wall 34a and the upper wall 34e, the center of the stylus will be precisely on the center line 47 through the mounting pin 36 and the locking pin 37, which of course also means the center line of the hole in the guide block through which the locking pin 37 extends.

The guide block opening or pathway 34 may be made by machining or by molding techniques. However, it is difficult to mold plastic with precision, and difficult to machine the irregular opening 34 from above with accuracy. It has been found that the preferred and most accurate method for forming the rear wall 34a and adjacent portions of upper wall 34e of the guide block 33 is that these surfaces be formed by the same drill bit or cutting tool used to form the hole through which the locking pin 37 extends. Thus, regardless of whether the initial forming of the pathway of the guide block is created by machining or molding, it is preferred that the rear portion of the pathway be not completely cut to its desired form so that the finishing of the rear and adjacent upper wall can be formed by a drill bit 60 which extends through the outer or lateral wall of the block 32 in forming the hole for the locking pin, as seen in FIGS. 7 and 8. This positive error and following procedure insures that a stylus 30, while engaging the rear wall 34a and upper wall 34e of a guide block 33 in centric position is exactly on the center line 47 of the mounting pin 36 and the locking pin 37.

The tip 60a of the drill bit utilized is curved to provide the desired curvature of the corner 34f of the medial wall. The guide block outer medial surface 35 is used as a reference surface in controlling the depth at which the tool tip 68a is inserted during the cutting operation. The metal pin 36 provides rigidity to the plastic block which makes the surface 35 preferable to the outer lateral block wall as a reference surface. Thus, this critical area of the guide block can be accurately formed in a single drilling or precision lathe operation.

As is explained in co-pending application Ser. No. 814,815, filed July 11, 1977, it is desirable that a set of average value guide blocks be formed having different wall curvatures for the corner 34f. This is accomplished by utilizing a set of drill bits 60 having tips 60a which correspond to the desired curvature corners 34f. The tip curves are preferably circular segments having radii larger than the radius of the tool 60. However, other curves with a changing, but larger radii than the tool radius, might be desired in some instances. The diameter of the tool 60 and hence the hole formed thereby is equal to the diameter of the stylus 30, FIG. 1, which moves within the guide block.

To insure that the locking pin 37 is properly positioned within the hole in the mounting block to which it extends, the pin is formed with a very accurate cylindrical configuration which fits snugly within the hole thereby providing precise alignment. The pin is held in a desired position by a set screw 39 extending through a wall of the block, rather than utilizing threads or some other locking arrangement.

As explained above, the locking pin 37 is employed when it is desired to lock the frames in centric position for simple hinging action. When such action is not needed, the pin may be removed so as not to interfere with movement of the stylus within the guide block opening. As explained in U.S. Pat. No. 4,034,475, Lee, mentioned above, a curve 90 corresponding to the curve of the upper or superior wall of the guide block may be formed on the outer or exterior wall of a guide block. Thus, when a representation of a patient's protrusive movement path is formed on a transparent sheet, as explained in U.S. Pat. No. 4,034,475, such sheet may be properly positioned against the upper frame aligned with a suitable reference surface and the guide block rotated so that the curve on the exterior of the block is aligned with the curve on the transparent sheet.

The use of a locking pin 37 interferes with this system in that the pin hole 76 extends through a portion of the area where the curve on the block would be located if there were no hole. Thus, to utilize the general system described in that earlier Lee patent, there is provided a separate reference plate 70, shown in FIG. 9. The plate is preferably made of light-weight plastic or metal and has a curve 72 formed thereon. The curve 72 corresponds or is parallel to the curve of the wall 34e within a particular guide block 32, when the plate is properly positioned on the exterior of the guide block. For this purpose, the plate 70 is provided with a short pin 74 on its back side which snugly fits within the hole 76 in the guide block through which the locking pin 37 is normally positioned. That is, the pin 37 is withdrawn and the pin 74 of the plate 70 is positioned therein. Further, a recess 78 is formed in the exterior wall corresponding to the shape of the plate 70 so that the plate 70 fits within the recess. An alignment pin 88 is precisely located in the recess 78 to mate with a corresponding precise hole 88a in the plate 70, so that the plate 70 is angularly oriented with respect to the curve of the upper wall 34e in the guide block. Thus, the curve 72 on the plate will accurately represent the path of the stylus 30 when moving in contact with the upper wall 34e in the guide block. The mounting pin 74 for the plate can be locked in position by the same set screw 39 utilized to clamp the locking pin 37.

In use of the articulator, the mounting plate 21 is secured to the mounting area 20 by a suitable fastener 20a with the sockets in the pins 21a receiving the dowels 25 to insure accurate positioning. A dental cast is then secured to the plate 21 by plaster using known techniques. An upper dental cast is mounted on the upper frame in a similar manner using a mounting plate (not shown) similar to the plate 21. A hole is formed in the forward portion 40 of the upper frame 12 for receiving a threaded fastener 40a for connection to such a mounting plate. Depending dowels 40b mate with holes in such a plate to accurately position the plate, as with plate 21.

FIG. 6 depicts the method in which the articulator of the present invention is tested for its accuracy. As mentioned above, one way to achieve interchangeability on articulators is to construct each one so that the mounting area of the upper frame is parallel to a high degree of accuracy to the mounting area of the lower frame, with a given spacing. A determination of this characteristic can be made by placing test blocks 52 onto the respective mounting areas of the upper and lower frames, and adjusting incisal pin 46 to the point where the mounting frames should be parallel. The test blocks are formed with suitable accurately positioned sockets (not shown) similar to that in the buttons 21a on the mounting plate 21 to position the blocks transversely, and are also formed to receive the fasteners 20a and 40a for attaching the blocks to the frames, as is done with dental cast mounting plates, where the mounting frames should be parallel. A thin feeler gauge is then utilized to determine if there are any spaces between the test blocks whose mating surfaces should uniformly touch. If there are spaces or inconsistencies beyond the allowed tolerances, the articulator is not sufficiently accurate to allow interchangeability. The test blocks 52 are precisely formed on their sides so that the front to rear and side to side alignment can be checked by observation or feel. Also, vertical sight lines 53 may be scribed on the blocks to further assist in checking alignment.

I claim:

1. A dental articulator comprising:
   a first frame having a pair of guide blocks mounted thereon;
   a second frame having a pair of spaced pedestals each supporting a spherical stylus, said styluses defining a hinge axis;
   each of said blocks having an opening formed therein for receiving one of the styluses, said openings each being formed by a curved rear wall, a curved upper wall, a curved medial wall, and a lateral wall for guiding movement of the styluses, said rear and upper wall of each of the guide blocks being engaged by a respective one of said styluses when the frames are in centric position; and
   means defining a circular hole drilled into the lateral wall of each of said blocks on a line which is collinear with said hinge axis when the styluses are in said openings and the frames are in centric position, said hole connecting with the opening in each of the blocks, the diameter of the drilled hole in the area of said rear wall being equal to the diameter of said stylus, the shape and size of the curved side walls of the hole being continuous with and equal to those of the rear and upper walls of the opening by virtue of their being formed at the same time in a single drilling operation.

2. The guide blocks of claim 1 including a mounting pin fixed in the medial wall of each of said blocks with said mounting pin being collinear with said hole in the lateral wall.

3. Dental apparatus comprising:
   a guide block for mounting on a frame of a dental articulator, said block having an opening therein for receiving a stylus mounted on a second frame of a dental articulator, said block having a hole through its lateral wall which is concentric with an axis through the center of a pair of said styluses when said frames are in centric position; and
   a plate with a pin attached thereto and extending perpendicular to the plate, said pin fitting snugly within said hole so that the plate is supported adjacent the outer lateral surface of said block, said plate having means forming a line on its outer surface which is parallel to the upper surface of said opening in said guide block when said plate is properly angularly oriented.

4. The apparatus of claim 3 wherein said block has means formed thereon for angularly orienting said plate so that said line on the plate is parallel to said guide block upper wall.

5. A method for manufacturing interchangeable dental articulators, each said articulator having a lower frame and an upper frame, said lower frame having a horizontal portion with a dental case mounting area thereon and a vertical portion joined to said horizontal portion, and a pair of styluses mounted on said vertical portion, said upper frame having a forward portion with a dental cast mounting area thereon and a rear portion having a hole therein to receive a pair of guide blocks which have openings for receiving said styluses, the method comprising the steps of:
   machining the mounting area of the lower frame;
   machining the upper surfaces of the vertical portion of the lower frame so that they are parallel to said lower frame mounting area, said lower frame horizontal and vertical portions being joined together as a one-piece unit when said machining is performed to a high degree of accuracy; and
   drilling the hole in the rear portion of the upper frame, machining the mounting area of the upper frame using said hole as a reference location in said machining such that the center line of said hole is parallel to a close tolerance to said upper frame mounting area.

6. The method of claim 5 wherein said horizontal portion and said vertical portion of said lower frame is of a one-piece construction.

7. The method of claim 5 wherein said horizontal mounting area and said upper surface of said vertical portion are machined during a single mounting in a milling machine.

8. The method of claim 5 wherein said stylus openings each include a rear wall and adjacent upper wall portions to be engaged by one of said styluses when the frames are in centric position, including the steps of drilling a hole into the lateral walls of each of said blocks which are collinear with said hole in said upper frame when the blocks are mounted in said upper frame, said hole in each of said blocks forming the rear and adjacent upper wall of each of sad openings.

9. The method of claim 6 wherein the openings in said guide blocks are initially formed with a positive error in the area of said rear wall so that the rear wall of said opening is finished by said drilling operation in said guide blocks.

10. The method of claim 9 wherein said guide block openings include a medial wall and a curved corner between said medial wall and said rear wall, and including the step of forming said curved corner wall with the tip of the drill during said step of drilling said guide block hole.

11. The method of claim 5 including:
   drilling dowel receiving alignment holes in and perpendicular to said lower frame mounting area and drilling stylus pedestal mounting holes in and perpendicular to said upper surfaces on said lower frame vertical portion, said lower frame holes being precisely spaced from and parallel to each other; and
   drilling dowel receiving alignment holes in and perpendicular to said upper frame mounting area, said upper frame dowel receiving holes being precisely spaced from end reference surfaces on the rear portion of said lower frame and from the centerline of said hole in the rear portion of the upper frame.

12. A method for manufacturing the lower frame of a dental articulator having a horizontal portion with a dental cast mounting area thereon, and a vertical portion attached to said horizontal portion and having an upper surface, comprising the steps of:
   machining a flat surface on said lower frame to form said mounting area;
   machining the upper surface of said vertical portion such that it is parallel to said mounting area to a high degree of accuracy, said machining being performed while said vertical and horizontal portions are a one-piece unit.

13. In a dental articulator, a pair of guide blocks mounted on one frame of the articulator, said blocks having an opening formed therein for receiving a pair of styluses mounted on a second frame of the articulator, said styluses defining a hinge axis, said openings each including a rear wall and an upper wall to be engaged by a respective one of said styluses when the frames are in centric position, a method of accurately making said rear wall and adjacent upper wall for each of said blocks comprising:

drilling a hole into a lateral wall of each of said blocks on a line which will be collinear with said hinge axis when the frames are in centric position, with the side wall of said drilled hole forming said rear wall and adjacent upper wall, the diameter of said hole drilled in the area of said rear wall being equal to the diameter of said stylus.

14. The method of claim 13 including forming each of said openings slightly smaller than it should be in the area of said rear wall and adjacent upper wall so that the rear wall and adjacent upper wall is completed by said drilling step.

15. The method of claim 13 or 14 wherein each of said guide blocks includes a medial wall adjacent said rear wall having a mounting pin fixed in the wall of the block on the side of said medial wall, with said mounting pin being collinear with said hole in the lateral wall.

16. The method of claim 13 wherein said drilling step is performed with a drill bit having a curved tip which forms a corner portion of a medial wall of said opening adjacent the rear wall, said curved tip being formed to produce the exact curvature on the corner which is desired.

17. The method of claim 16 wherein said curved tip has a curvature which produces a circular curve, with the radius of said circular curve being larger than the radius of the drill bit.

* * * * *